United States Patent [19]

Stovicek

[11] Patent Number: 5,173,110
[45] Date of Patent: Dec. 22, 1992

[54] ANTIFOULING COMPOSITION
[75] Inventor: Pavel Stovicek, Coquitlam, Canada
[73] Assignee: Waitomo Industrial Investments Ltd., British Columbia, Canada
[21] Appl. No.: 850,769
[22] Filed: Mar. 13, 1992

Related U.S. Application Data

[60] Continuation-in-part of Ser. No. 631,652, Dec. 21, 1990, Pat. No. 5,096,488, which is a division of Ser. No. 304,769, Jan. 19, 1989, Pat. No. 4,990,547, which is a continuation-in-part of Ser. No. 153,010, Feb. 8, 1988, Pat. No. 4,866,106.

[51] Int. Cl.$^5$ ................................................ C08K 5/19
[52] U.S. Cl. ............................. 106/18.32; 106/15.05; 71/67; 424/405; 424/408; 424/501; 523/122; 524/236; 428/255; 428/411.1; 428/537.1; 428/688
[58] Field of Search ............. 106/15.05, 18.32; 424/405, 408, 501; 71/67; 523/122; 524/236; 428/255, 411.1, 537.1, 688

[56] References Cited

U.S. PATENT DOCUMENTS

| | | | |
|---|---|---|---|
| 3,854,960 | 12/1974 | Plum et al. | 106/18.31 |
| 4,128,429 | 12/1978 | Wyant et al. | 106/18.32 |
| 4,273,833 | 6/1981 | DeLong | 523/122 |
| 4,631,302 | 12/1986 | Supcoe et al. | 523/122 |
| 4,661,400 | 4/1987 | Guglielmo, Sr. | 428/255 |
| 4,675,051 | 6/1987 | Baxter | 106/16 |
| 4,687,792 | 8/1987 | Russell et al. | 523/177 |
| 4,752,629 | 6/1988 | Proudlock et al. | 523/122 |
| 4,866,106 | 9/1989 | Pellow et al. | 523/122 |
| 4,990,547 | 2/1991 | Stovicek | 424/405 |
| 5,096,488 | 3/1992 | Stovicek | 106/18.32 |

FOREIGN PATENT DOCUMENTS

| | | |
|---|---|---|
| 53-124538 | 10/1978 | Japan . |
| 60-210677 | 10/1985 | Japan . |
| 60-217274 | 10/1985 | Japan . |
| 62-084167 | 4/1987 | Japan . |
| 62-232470 | 10/1987 | Japan . |
| 63-008462 | 1/1988 | Japan . |
| 63-081177 | 4/1988 | Japan . |
| 63-161041 | 7/1988 | Japan . |

Primary Examiner—Karl Group
Assistant Examiner—Anthony J. Green
Attorney, Agent, or Firm—Darby & Darby

[57] ABSTRACT

An antifouling coating composition useful for coating fish netting, boat hulls, lumber, roof shingles and the like to prevent the growth of algae. The composition comprises a solution of an epoxy resin containing a dialkyldimethyl ammonium compound or an alkylbenzylmethyl ammonium compound or combinations thereof. The invention also relates to articles coated with the composition to prevent the formation of algae thereon.

13 Claims, No Drawings

ANTIFOULING COMPOSITION

RELATED APPLICATIONS

This application is a continuation-in-part of co-pending U.S. Pat. application Ser. No. 631,652, filed Dec. 21, 1990; which, in turn, is a division of U.S. Pat. application Ser. No. 304,769, filed Jan. 31, 1989, now U.S. Pat. 4,990,547, issued Feb. 5, 1991; which, in turn, is a continuation-in-part of U.S. Pat. application Ser. No. 153,010, filed Feb. 8, 1988, now U.S. Pat. 4,866,106, issued Sep. 12, 1989.

FIELD OF THE INVENTION

This invention relates to an antifouling coating composition. The composition is useful for coating equipment to be submerged in the sea, for example, fish nets and boat hulls, but also finds use for coating lumber and roof shingles and the like exposed to much rain and subject to algae growth.

DESCRIPTION OF THE PRIOR ART

The growth of algae on structures, for example, on boat hulls, on fishing nets, on roofs, on patios and on lumber is unsightly. There are, however, more important failings. The hull of a boat is considerably less efficient when coated with algae; the drainage of a roof can be adversely affected by the presence of algae; and patios, balconies and the like can become slippery when wet if algae are present. In industry, fouling and plugging of water pipes, particularly in cooling systems, can occur with algae growth, for example, in the pulp and paper mill industries. The warm temperatures in cooling system waters make ideal conditions for algae growth.

A hull of a boat or a walkway can be scrubbed to remove the algae but, for example, in the case of a boat, this involves removing the boat from the water and also a considerable amount of hard work. As a result, chemical approaches have been used. Compounds such as chlorine, organic mercury compounds, chlorinated phenols, organic bromine compounds, metallic copper and organic tin and sulphur compounds have all been used in an attempt to reduce the growth of algae.

In the growing of fish in pens there is a marked need for a biodegradable antifouling coating for the nets that are used to pen the fish. The coating is required to prevent the growth of marine organisms, which restrict the flow of fresh tidal water through the net.

This need has been met by the use of antifouling coatings containing heavy metals, for example, metallic copper, organic tin and mercury compounds and the like. However, heavy metal coatings are environmentally undesirable, particularly in the marine environment. It has been shown that they have an adverse effect upon shellfish beds and other coastal marine life, even in trace amounts. As a result, the use of heavy metals is now illegal in some jurisdictions.

In the lumber industry, wood preservatives have been used to combat fungal growth on lumber having a very high moisture content. Until recently, pentachlorophenols were used, but these are now regarded as environmentally unsafe. Other preservatives such as mixtures of quaternary ammonium compounds and 3-iodo-2-propynyl butyl carbonate, copper 8-quinolinolate, and borax-sodium carbonate mixtures have proved unsatisfactory for such reasons as poor efficacy in wet climates, rapid leaching due to high solubility and brown staining. Accordingly, there is a need to develop a coating for lumber which is effective over the long term against fungal growth.

Yet a further use of antifouling compositions is in hospitals where medically sterile environments are required if S. aureus infections are to be avoided, and on concrete or over soil.

However, no system developed so far is believed to be ideal. The most popular, the use of chlorine, is limited first by the toxicity of chlorines and chlorine-containing compounds. To be effective, chlorine requires quite large doses, making its use economically unattractive. Furthermore, it is a highly reactive compound, making it difficult to store and, when applied, it interacts with other compounds in the environment, reducing its effectiveness against algae.

Simply stated, the prior art fails to teach coating compositions, effective over a considerable period, to destroy algae.

SUMMARY OF THE INVENTION

The object of the present invention is to provide a coating composition providing long-lasting antifouling properties. Accordingly, the present invention is an antifouling coating composition comprising:
 a settable resin; and
 a non-metallic algicide that does not react with the resin.

The settable resin may be an epoxy resin, for example one curable by a polyamide.

This encapsulation of the highly soluble quaternary ammonium compounds retards their migration to the surface of the coating, thereby enabling the coating to retain biocidal activity for a long period, over one year, even in a moist or wet environment.

The compositions may contain up to 10% by weight of filler. Exemplary fillers are calcium carbonate, talc, silica and alumina. Such fillers serve to increase the bulk of the coating composition.

The particularly surprising aspect of the present invention is the finding that a solution containing a substantial amount of quaternary ammonium compounds can be formed which has an almost indefinite shelf life. In addition, the compositions have good coating and film-forming ability as well as substantial flexibility.

In order for the encapsulation to be considered satisfactory, the polymer must retain the quaternary ammonium compound for at least one year in water at ambient temperatures.

DETAILED DESCRIPTION OF THE INVENTION

The settable epoxy resins which may be used in accordance with the invention include the following compounds:

Bisphenol "A"

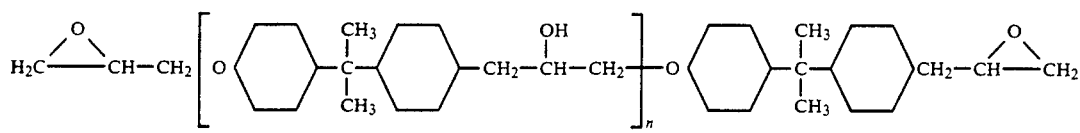

Epoxy Novolac

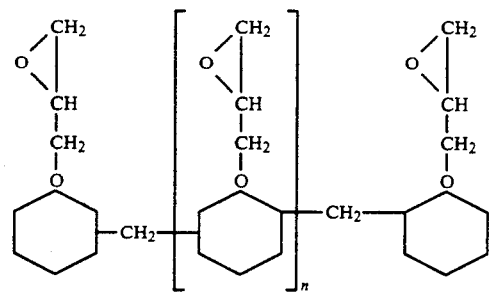

Polyglycol Epoxy

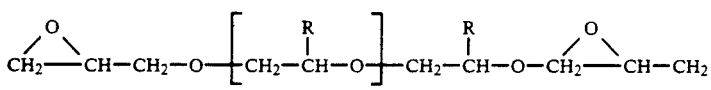

or mixtures of such epoxy resins, such as blends of
Bisphenol A + Novolac + Polyglycol;
Bisphenol A + Novolac;
Bisphenol A + Polyglycol; and
Novolac + Polyglycol.

The hardeners which may be used are well known to those skilled in the art and include: polysulfides, aliphatic amines, polyamides, amidoamines, aromatic amines, dicyandiamide, and drides, melamine-formaldehyde, urea formaldehyde, phenol formal. dehyde, amine adducts, aminoethyl piperazines, methylene dianiline, and diaminodiphenyl sulfone.

Thixotropic agents such as fumed silica and polar additives such as glycols may also be used. In addition, reactive diluents such as glycidyl ether of $C_{12}$, $C_{14}$ alcohols, o-cresyl glycidyl ether, butyl glycidyl ether, and difunctional epoxy polyglycols may be added.

Solvents for epoxy resins include ketones such as dimethyl ketone, methylethyl ketone, methylpropyl ketone, and methylbutyl ketone. The amount used depends on the desired viscosity of the finished composition.

Solvents for the hardeners include xylene, toluene, and other well known mainly aromatic solvents.

The amounts of such materials used are conventional and may readily be determined by those skilled in the art. Where ketones are used as the solvent, higher amounts of the quaternary ammonium compound are desired, due to the rapid migration of the algicide to the surface Fillers and colorants may be added as desired.

The preferred non-metallic algicides are dialkyldimethyl ammonium compounds, preferably the chlorides and the acetates. These are generally from 2 to 50% by weight of the solids in the composition, excluding fillers and colorants. The aforementioned compounds can be used alone or in combination with N-alkylbenzylmethyl ammonium chloride, bromide, or acetate. In both instances, they have preferably from 8 to 18 carbon atoms in each of the long chain alkyl groups.

Specific examples of the dimethyldialkyl ammonium compounds are dioctyldimethyl ammonium chloride, didecyldimethyl ammonium chloride, didodecyldimethyl ammonium chloride, octyl-decyldimethyl ammonium acetate, decyldodecyldimethyl ammonium chloride, and dihexadecyldimethyl ammonium acetate. Examples of the alkylbenzylmethyl ammonium compounds are decyldimethylbenzyl ammonium chloride, dodecyldimethylbenzyl ammonium chloride, dodecyl dimethylbenzyl ammonium acetate, tetradecyldimethylbenzyl ammonium chloride, hexadecyldimethylbenzyl ammonium bromide, octadecyldimethylbenzyl ammonium chloride, quaternary salts produced from natural sources such as cocodimethylbenzyl ammonium chloride, oleyldimethylbenzyl ammonium chloride, canola dimethyl benzyl ammonium chloride, or mixtures thereof.

The dialkyldimethyl ammonium compound may be admixed with up to 3.5 times as much by weight of benzalkonium chloride. Preferably, the ratio of the benzalkonium compound to the dialkyl should be about 1:2 by weight.

If a filler is employed in the formulation, this is added to the quaternary ammonium compound prior to its introduction into the diluted latex.

The formulation of the invention may be applied to the substrate by any of the conventional methods. For example, for fish net treating, dipping is employed. For other applications, dipping, spraying and brushing can be used.

In order to demonstrate more clearly the instant invention, the following examples are set forth:

Epoxy-containing formulations are illustrated by formulas K, L, and M below. A highly water-resistant epoxy (for example, that available under the trademark Novolac Den 444 from Dow Chemical) can be mixed with a variety of solvents to form a new composition referred to as part A in these formulations. All of the components of this part are thoroughly dispersed before use.

Polyamine and polyamide hardeners, such as those available from Henkel under the trademarks Versamine 115 and Versamide 125 and 140, can be dispersed in a solvent (for example, xylene) and then mixed with the above algicides to form novel water-free antifouling dispersions referred to as part B in the formulations below. Parts A and B can be mixed to form antifouling compositions which set due to the reaction between the epoxy bases and the polyamides. Various types and amounts of solvents are chosen to complement the viscosity characteristics of the amide hardener and the epoxy resin. Solvents can be evaporated as the reaction proceeds. Parts A and B are mixed in the proportions of 1 to 1 for all of the formulations. The ratio is dependent on stoichiometric requirements plus flexibility and adhesion requirements. After waiting 10 to 15 minutes, the product of A and B can be used to coat the desired substrate. Usable application times are typically 2 hours. Full cure of the paint is in 36 hours at a temperature of 10° C. or 24 hours at a temperature of 25° C.

| Composition of Clear* Epoxy-Antifouling Compositions in Parts by Weight | | | |
|---|---|---|---|
| | Formula K | Formula L | Formula M |
| Part A | | | |
| Novolac Den 444 | 100 | 100 | 100 |
| Methylisobutyl ketone | 70 | 70 | 70 |
| Propylene glycol methylether | 40 | 40 | 40 |
| Xylene | 80 | 0 | 80 |
| Urea formaldehyde | 1.5 | 1.5 | 1.5 |
| Fungitrol 11** | 4–8 | 4–8 | 4–8 |
| Part B | | | |
| Versamine 115 | 82 | 0 | 82 |
| Xylene | 35 | 17 | 7 |
| Versamide 140 | 0 | 67 | 0 |
| Quaternary ammonium compound | 0 | 4–200 | 4–200 |
| Dow Corning 6020 Silane | 1–5 | 1–5 | 1–5 |

*Fillers and colorants can be added to part A as required.
**Trademark of Nuodex Inc., Piscataway, NJ, for trichloromethyl thiophthalimide.

In the above formulations, the solvents are the menthol-isobutyl ketone; the propylene glycol methylether serves as an extender; and the urea formaldehyde is a film-former which reacts with the epoxy resin. The Fungitrol 11 serves to broaden the spectrum of the algicidal and microbiocidal activity of the formulation. The Dow Corning 6020 Silane assists in making the coating water-repellent, but does not prevent the quaternary ammonium compounds from migrating to the surface of the finished coating.

To demonstrate the efficacy of the formulation, formulas K, L, and M may be replicated using specifically 2 parts Fungitrol 11 and 2 parts of the Dow Corning 6020 Silane. The quaternary ammonium compounds in formulas L and M, respectively, were 120 parts of Barquat MB 80 and 160 parts of Bardac 2280 (trademarks of Lonza Inc., Fair Lawn, NJ). Barquat MB-80 is an 80% active solution of N alkyl ($C_{14}$ 50%; $C_{12}$ 40%; $C_{16}$ 10%) dimethyl-benzyl ammonium chloride. Bardac 228 of didecyl dimethyl ammonium chloride.

These formulations were applied to the hull of a steel boat which was immersed in the ocean at a temperature of from 14° to 17° C. for one year. Upon inspection, the coated areas where formulas K and L were applied were fouled with marine life, algae, and barnacles. The areas coated with formula M were also fouled, but to a minimal extent. When running the boat to a speed of approximately 2 knots, the fouling on the surfaces coated with formulas L and M peeled away from the coating, while the fouling on the areas coated with formula K tenaciously adhered to the coated surface. This test clearly shows the efficacy of the antifouling compositions of the invention.

The compositions are characterized by the absence of chemical reaction between the algicide and the carrier. The algicide slowly migrates to the surface to give a long term, reliable antifouling effect.

The quaternary ammonium chloride algicides leaching into the surrounding waters from the polymer carrier are degraded by oxygen and water, unlike highly toxic metal-containing anti-fouling agents. Algicides of the N-trichloromethyl thiophthalmide type, which are generally available under the trademark Folpet, leach into the surrounding waters and are slowly hydrolyzed. The chlorine substituents are combined with marine cations such as sodium, potassium, calcium, and magnesium to form harmless salts.

The algicides act as plasticizers for the polymer carriers, making the latex-containing coatings particularly suitable for flexible substrates by inhibiting chipping of the polymer from the substrate (for example, fish nets). Epoxy-containing coatings are particularly suitable for rigid sub. strates, such as marine buoys or boat hulls. Algicides impregnated in epoxy carriers leach less rapidly than algicides contained in latex carriers.

We claim:

1. An antifouling coating composition comprising an organic solution of an epoxy resin, an epoxy hardener, and a non-metallic algicide containing a quaternary ammonium compound having either methyl groups and two alkyl groups or methyl groups, an alkyl group and a benzyl group, said algicide being encapsulated in said resin and being capable of being leached from said composition during submersion.

2. The composition of claim 1 wherein the quaternary ammonium compound has up to 18 carbon atoms in the alkyl chain.

3. The composition of claim 1 including a filler.

4. The composition of claim 3 wherein the filler is selected from calcium carbonate, talc and silica.

5. The composition of claim 1 wherein from 2 to 50 parts by weight of the non-metallic algicide based on solids is present.

6. The composition of claim 1 wherein the quaternary ammonium compound is a dialkyldimethyl ammonium chloride containing from 8 to 16 carbon atoms.

7. The composition of claim 1 wherein the organic solvent is a ketone.

8. The composition of claim 7 wherein the ketone is dimethyl ketone, methylethyl ketone, methylpropyl ketone, or methylbutyl ketone.

9. The composition of claim 1 wherein the epoxy resin is a novolac epoxy, a polyglycol epoxy, a bisphenol A epoxy, or a mixture thereof.

10. The composition of claim 1 wherein the epoxy hardener is a polyamide or a modified amine.

11. A coated article which comprises a substrate coated with the composition of claim 1.

12. The coated article of claim 11 wherein the coated article is a fish net.

13. The coated article of claim 11 wherein the coated article is wood or concrete.

* * * * *